(12) United States Patent
Hölzle et al.

(10) Patent No.: US 6,171,858 B1
(45) Date of Patent: Jan. 9, 2001

(54) PROSCESS FOR DETERMINING THE PHOTOTOXICITY AND/OR PHOTOSENSITIVITY OF SUBSTANCES OR MIXTURES THEREOF, AND USES THEREOF

(75) Inventors: Erhard Hölzle, Hamburg; Martin Rosenbruch, Düsseldorf; Gerd Plewig, Müchen; Percy Lehmann, Düsseldorf; Norbert J. Neumann, Sturmstr. 101, D-40229 Düsseldorf, all of (DE)

(73) Assignee: Norbert J. Neumann, Dusseldorf (DE)

( * ) Notice: Under 35 U.S.C. 154(b), the term of this patent shall be extended for 0 days.

(21) Appl. No.: 09/117,797

(22) PCT Filed: Feb. 5, 1997

(86) PCT No.: PCT/EP97/00508

§ 371 Date: Mar. 11, 1999

§ 102(e) Date: Mar. 11, 1999

(87) PCT Pub. No.: WO97/31266

PCT Pub. Date: Aug. 28, 1997

(30) Foreign Application Priority Data

Feb. 12, 1996 (DE) .............................. 196 06 207

(51) Int. Cl.[7] .............................. C12N 5/00; C12N 5/06; C12Q 1/00
(52) U.S. Cl. .......................... 435/349; 435/350; 435/351; 435/352; 435/325; 435/4; 424/581; 424/582
(58) Field of Search ................................. 435/349, 350, 435/351, 352, 325, 4; 424/581, 582

(56) References Cited

U.S. PATENT DOCUMENTS 5,405,369   4/1995   Selman et al. .

FOREIGN PATENT DOCUMENTS

| 628736 | 3/1982 | (CH) . |
| 3038255 | 5/1982 | (DE) . |
| 3802780 | 8/1989 | (DE) . |
| 3939411 | 6/1991 | (DE) . |
| 4404977 | 2/1996 | (DE) . |
| 0497399 | 8/1992 | (EP) . |
| 2215043 | 9/1989 | (GB) . |
| 85/05184 | 11/1985 | (WO) . |
| 93/01272 | 1/1993 | (WO) . |
| 94/02847 | 2/1994 | (WO) . |

OTHER PUBLICATIONS

Kagan, J., et al, *J. of Natural Products* 46:646–650 (1983).
Goldberg, S. J. et al, *Pediatric Research* 32:23–26 et al (1992).
Roberts, W. G., et al, *Cancer Research* 52:924–930 (1992).
N.J. Neumann et al, *Photo hen's egg test: a model for phototoxicity*, British. J. Dermatol. 136: 326–330, (1997).
Holzle et al. Biologic Effects of Light 1995, Proceedings of a Symposium (1996), Meeting Date Oct. 9–11, 1995, pp. 168–173.*
Cortes et al., Journal of Photochemistry and Photobiology B: Biology, vol. 9, No. 2, pp. 229–234, 1991.*

* cited by examiner

Primary Examiner—Leon B. Lankford, Jr.
Assistant Examiner—Susan D. Coe
(74) Attorney, Agent, or Firm—Connolly Bove Lodge & Hutz LLP

(57) ABSTRACT

A process is disclosed for determining the phototoxicity and/or photosensitivity of substances or substance mixtures, involving putting the chemical substance or substance mixture into contact with a non-human vertebrate embryo or tissues or tissue components of a vertebrate embryo, except for human skin cell cultures, whereby, following the contact, there is also a treatment with electromagnetic radiation ranging from 1 mm to 200 nm, followed by evaluation of the pathology of the embryo, tissue or cell; also disclosed is the use of a non-human vertebrate embryo or tissues or tissue components of such an embryo, except for human cell cultures, for purposes of determining the phototoxicity and/or photosensitivity of chemical substances/substance mixtures.

18 Claims, No Drawings

PROSCESS FOR DETERMINING THE PHOTOTOXICITY AND/OR PHOTOSENSITIVITY OF SUBSTANCES OR MIXTURES THEREOF, AND USES THEREOF

The invention relates to a process for determining the toxicity of electromagnetic radiation, the phototoxicity and/or photosensitivity of substances or substance mixtures as well as use of said process.

Phototoxicity as defined in the present invention refers to an impairment of the local tolerance brought about by electromagnetic radiation within the range from 1 mm to 200 nm as the result of exposure to infrared light, visible light or ultraviolet radiation.

In particular, a phototoxic reaction refers to a reaction in which radiation energy and/or sensitizing substances penetrate the skin in an exogenic or endogenic manner and then cause photodermatosis. In this process, such phototoxic substances not only absorb UV radiation, but they can also be chemically altered by it. They are capable of absorbing in various radiation ranges, as a function of their chemical structure. It is assumed that there is a corresponding correlation between the quantity of radiation energy and the substance struck by the radiation. A small amount of energy and a large amount of substance have the same effect as a small amount of substance and a large amount of radiation energy. At a maximum congruence of the two reaction parameters, the phototoxic reaction will be particularly intense. As a rule, a phototoxic reaction appears approximately 8 to 12 hours after the initial exposure. Now and then, this can also take place earlier. Common symptoms are a very pronounced reddening associated with blistering and subsequent post-inflammatory pigmentation. Even a sunburn can be seen as a phototoxic reaction.

In contrast to a phototoxic reaction, a photoallergic reaction is defined as a reaction which occurs even in response to smaller quantities of radiation and just a small amount of activatable substance. Moreover, this is not dose dependent. The mechanism here is the same as that of an allergy, whereby the foreign substance altered by the radiation can turn into the hapten, which then combines with the protein to form an allergen. A photo-allergic reaction is usually manifested in the form of eczema. It appears between 48 and 72 hours after the initial exposure to the sun. As we know from the developmental mechanism of allergies, they never occur after the first exposure, since this is the instance that leads to the formation of antibodies. Photoallergic reactions are not restricted to the areas of skin exposed to the radiation. As a spreading phenomenon, they also occur on other parts of the body which have not been irradiated. As compared to the absorption spectrum, the action spectrum is shifted more towards the long-wave range. Particularly problematic photoallergic reactions are reactions to chemically related substances such as, for example, para substances. The amino-, hydroxy- and nitro-group, substituted in the para position on the phenyl ring, is the typical technical-structural feature.

It is a known practice to employ chicken embryos in order to study the toxicological properties of test substances. For this purpose, the substance specimens are normally applied to the embryo via the extraembryonal blood vessel system.

Two recent scientific publications from the literature can be mentioned as representative of the common use of chicken embryos as a model system for pharmacological (Roberts, W. G and Hasan, T. in CANCER RESEARCH, volume 52, pages 924 through 930, 1992) or toxicological test series (Goldberg, S. J.; Dawson, B. V.; Johnson, P. D.; Hoyme, H. E. and Ulreich, J. B., PEDIATRIC RESEARCH, volume 32, pages 23 through 26, 1992).

The publication by Roberts and Hasan describes the pharmacological/pharmacotopological properties of photodynamic agents in proliferating vascular and non-vascular tissues in chicken embryos. The chicken embryogenesis serves as a model system for the angiogenesis in solid tumors.

The publication by Goldberg et al., in contrast, describes the use of chicken embryos as a method to examine the teratogenicity of substances, particularly dichloroethylene. The above-mentioned publications, however, neither suggest nor anticipate the approach of studying phototoxic and/or photosensitive substances in chicken embryos.

Up until now, only an animal model or cell systems have been available for studying potentially phototoxic or photosensitive substances.

The animal model is the "Draize test" which detects the irritation caused by photo-toxic substances in the eye of rabbits. Its use is limited, not only due to cost considerations but also particularly from an animal-rights standpoint.

The cell systems available, that is to say, bacteria, yeast and other eucaryotic cells, are likewise inadequate as models for phototoxicity since the physiological marginal conditions of the phototoxic or photosensitive substance behavior cannot be adequately duplicated.

The present invention has the objective of creating a technically simple method for testing potentially phototoxic substances. On the one hand, this test should take the physiological conditions on the skin into account and, on the other hand, also meet future legislative plans and ethical considerations. This objective is achieved by the features of claim 1.

Thus, the present invention relates to a process for determining the phototoxicity and/or photosensitivity of substances and/or substance mixtures, involving putting the chemical substance or substance mixture into contact with non-human vertebrate embryos or tissues or tissue components of a vertebrate embryo, except for human skin cell cultures, whereby, following the contact, there is an additional treatment with radiation ranging from 1 mm to 200 nm, followed by evaluation of the pathology of the embryo, tissue or cell.

According to a preferred embodiment of the present process, prior to contact, eggs of the Aves class, that is to say, birds, are incubated as the form containing vertebrate embryos and, at a later point in time after the embryonal gastrulation, some of the egg white is removed from the egg via at least one opening and, if applicable, further incubation takes place and another opening is provided in the upper section of the egg shell for purposes of the radiation.

Even though it is fundamentally possible to employ any non-human vertebrate embryo or a tissue or a tissue component of a vertebrate embryo, except for human skin cell cultures, practical considerations have proven it to be advantageous to give preference to the use of incubated eggs of the Aves class, in other words, birds. Examples of these are the eggs of ostriches, rheas, emus, kiwis, tataupas, gallinaceous birds, hoatzins, quail, pigeons, sand grouse, rails, jacanas, cranes, bustards, gulls, wading birds, auks, divers, grebes, penguins, petrels, duck-like anseres, steganopods, glossy ibises, flamingos, diurnal raptors, cuckoos, turacos, parrots, doves, kingfishers, bee-eaters, hoopoes, hornbills, owls, nightjars, swifts, hummingbirds, mousebirds, trogons, toucans, barbets, honey guides, woodpeckers and passerine birds. As incubated eggs, preference is given to eggs of the Galliformes order, that is to say, gallinaceous birds, whereby special preference is given to eggs of chickens, or else turkeys.

The period of incubation normally depends on the development time of the embryo in question.

According to a preferred embodiment of the present invention, the egg is provided with at least one opening after the first incubation of the eggs. This opening should preferably be at least of such a size that it allows part of the egg white to be removed through the opening. This is preferably done in such a way that part of the egg white, preferably 5 to 10 ml of the egg white present, is removed by means of a suction device, preferably a pipette such as, for instance, an Eppendorf pipette.

Following this aspiration procedure, another opening is made in the upper section of the eggshell so that later the radiation procedure can be carried out. This is normally done in such a way that a mechanical device is used to create another, this time larger, opening in the eggshell which can be accomplished, for instance, by means of a sharp cutting or milling instrument. After the second opening has been cut into the upper section of the eggshell, this opening is closed again and the egg is put back into the incubator. A common means is employed to close the opening, whereby preference is given, for example, to the use of a foil containing metal or to a material containing organic materials. Examples of these are sheets made of plastic, aluminum or composite films as well as appropriate wax plugs. If applicable, incubation is carried out again.

Following this incubation, the substances to be tested are applied, preferably on the fourth day of incubation, whereby these chemical substances/substance mixtures can be biologically active substances such as, for instance, cosmetics, pharmaceuticals, herbicides or insecticides. Furthermore, these chemical substances/substance mixtures can be light-protection agents for technical products as well as for cosmetic or pharmaceutical compositions, which are also known by the name UV filters.

The treatment of the embryo or tissues or tissue components of this embryo with chemical substances or substance mixtures normally takes place by means of electromagnetic radiation within the range from 1 mm to 200 nm, which normally refers to the spectrum encompassing infrared light, visible light and ultraviolet radiation.

However, preferably, the treatment is done with UV radiation having a wavelength smaller than 400 nm, particularly wavelengths between 250 nm and 400 nm, that is to say, for the most part involving UV-A radiation having a wavelength between 315 and 400 nm, or alternatively involving UV-B radiation having a wavelength ranging from 280 nm to 315 nm.

According to another preferred embodiment, the above-mentioned treatment is carried out with electromagnetic radiation in the infrared range; this is done is a known manner employing infrared radiation emitters, in the same manner as color filters or a prism can be used in the visible spectrum in order to set the appropriate wavelengths. When it comes to the spectrum of ultraviolet light, there are numerous sources of radiation such as, for example, mercury-vapor lamps, xenon-super-pressure lamps, sodium-vapor lamps, hydrogen or deuterium lamps as well as low-pressure discharge tubes filled with noble gas. Moreover, tungsten lamps or halogen lamps are also employed as UV radiation emitters as well as appropriate lasers.

When UV radiation emitters are used, it is common practice to employ radiation levels of 1 $mJ/cm^2$ to 100 $J/cm^2$. The upper value corresponds to the maximum UV-B dose, while the lower value corresponds to the minimum UV-A dose. Preference is given to the use of 5 to 10 $J/cm^2$ of UV-A, particularly 5 $J/cm^2$.

The contacting—according to the invention—of the chemical substance with the tissue or tissue components, preferably with the chorioallantoic membrane, especially the yolk vessel membrane, of the embryo takes place immediately or else this contact can be made up to 24 hours later.

According to a preferred embodiment, the macroscopic and/or microscopic embryonal pathology, in turn, is evaluated either immediately or within a period of up to 96 hours, preferably, however, after 5 minutes up to 24 hours. Within the scope of the above-mentioned evaluation of the macroscopic and/or microscopic embryonal pathology, the death of the embryo, the hemorrhaging, the membrane discoloration or the tissue or cell pathology are examined.

The present invention also has the objective of employing a non-human vertebrate embryo, a tissue or a tissue component of such an embryo, except for human skin cell cultures, in order to determine the phototoxicity and/or photosensitivity of chemical substance/substance mixtures.

The present invention will be illustrated in greater detail below with reference to embodiments. In this context, all of the figures are expressed as a percentage or as a percent-by-weight.

For purposes of carrying out the process according to the invention, two compounds having well-known phototoxic properties are employed, namely, 8-methoxypsoralen and hematoporphyrin. Promethazine and ciprofloxacin were used in order to evaluate the phototoxic properties by means of the process according to the invention.

For this purpose, first a non-toxic concentration of the above-mentioned substances and a non-toxic dose of UV-A radiation had to be defined by means of experiments. To this extent, the process according to the invention is conducted similarly to the hen's-egg test and serves to determine the non-toxic active dose of a test substance. A preliminary experiment showed that a UV-A radiation value at 5 $J/cm^2$ does not have any macroscopic pathological effects on the yolk sac. With the process according to the invention, a 10-time lower concentration was selected in order to apply a non-toxic active dose of the test substance to the yolk sac and to reliably rule out toxic reactions. Only in one case, that is, in the presence of ciprofloxacin, was a non-toxic concentration used which is clinically employed for intravenous injections.

The second phase of the process according to the invention is an evaluation in the sense of a 2×2 factorial test design with the factors "irradiation" and "substance application" and the stages "yes" and "no", as can be seen in the overview presented below.

| | Substance application (non-toxic concentration) | |
|---|---|---|
| radiation | yes | no |
| yes | $n_1$ – 12 | $n_2$ – 12 |
| no | $n_3$ – 12 | $n_4$ – 12 |

After 24 hours, the following parameters were evaluated: death of the embryo, semiquantitative membrane discoloration and hemorrhaging. This was done as follows: fertilized white leghorn eggs (of the type Shaver Starcross 288A, from Lohmann Tierzucht GmbH, a breeding company in Cuxhaven, Germany) were incubated in a horizontal position in a commonly employed incubator at 37.5° C. [99.5° F.] and 65% relative humidity. After 3 days of incubation, all of the eggs were candled in order to sort out those that were defective. Without damaging the shell membrane, a hole was drilled into the shell through which 5 ml of egg white were withdrawn for purposes of lowering the embryo and the yolk sack surrounding it. Subsequently, a window measuring 1.5 cm ×2.5 cm was sawed out of the eggshell. The eggs were covered with a suitably dimensioned piece of wax and then returned to the incubator. On day 4 of the incubation, only those eggs with normally developed embryos and blood vessel systems were used for the testing.

The following test substances were applied: 8-methoxypsoralen (8-MOP) $10^{-3}$ molar in a physiological saline solution, hematoporphyrin $10^{-5}$ molar likewise in a physiological saline solution (0.9%-sodium chloride solution), promethazine $10^{-3}$ molar in a physiological saline solution and ciprofloxacin $6.035\times10^{-3}$ molar in a physiological saline solution. The 2×2 factorial test design was employed for each test substance. Each time, an Eppendorf pipette was used to apply 500 $\mu$l of the test substance to a sample group consisting of 12 eggs and subsequently these were irradiated by a 5 $J/cm^2$ UV-A radiation emitter (320–420 nm, Philips TL 09/40W, of Hamburg, Germany). In each case, 12 eggs served as the controls as follows: without the substance, with 500 $\mu$l of a physiological saline solution or else with 500 $\mu$l of a physiological saline solution in combination with exposure to a 5 $J/cm^2$ UV-A radiation emitter. An evaluation was carried out immediately afterwards, as well as after 5, 15, 30 and 45 minutes and 1, 2, 4, 6, 8, 10 and up to 24 hours after their irradiation. During this time, the death of the embryo and, semi-quantitatively, the discoloration of the membrane and hemorrhaging were determined on the basis of a 4-point-scale.

The following classification was employed here:
Step 0: no visible membrane discoloration/hemorrhaging;
Step 1 (slight): barely visible membrane discoloration/ hemorrhaging;
Step 2 (moderate): visible membrane discoloration/ hemorrhaging, structures are partially blurred;
Step 3 (severe): visible membrane discoloration/ hemorrhaging, structures are completely blurred.

The above-mentioned changes were recorded by means of a macroscope type M 420 manufactured by Leitz Meβtechnik GmbH, an instrument company in Wetzlar, Germany. In order to be able to analyze the results statistically, non-parametric tests were employed. For the membrane discoloration parameters and for the hemorrhaging, the contingency table test for special categories was employed (a version of the KruskalWallis Test, modified for ordered categories). The death rates were analyzed by means of the Fischer contingency table test. Consequently, three statistical tests were calculated for each compound. Taking into consideration the number of tests and in order to compensate for the increased probability of finding a significant result, the $\alpha$-level was adapted ($\alpha^*$). Therefore, each of the three individual tests was carried out at a significance level of $\alpha^*=0.05/3$, that is to say, 0.0167.

Findings

Hematoporphyrin

In the case of hematoporphyrin (HP), considerable morphological changes were observed, with a maximum after 12 hours. After 24 hours,
75.0% (n=9) of the yolk sacs exhibited severe discoloration of the membrane,
16.7% (n=2) exhibited a moderate and
8.3% (n=1) a slight discoloration of the membrane with substances that had been treated with HP as well as with UV-A radiation.

In contrast to this, the control measurements displayed only slight or moderate membrane discoloration (exclusively with the use of HP,
33.3% (n=4) exhibited slight and
25.0% (n=3) moderate membrane discoloration; in the control group, which was only treated with a physiological saline solution and UV-A, the following was observed:
50.0% (n=6) exhibited slight membrane discoloration and
25.0% (n=3) moderate membrane discoloration;
finally, in the case of the comparison group treated exclusively with a physiological saline solution,
50.0% (n=6) of the membranes were slightly and
16.7% (n=2) moderately discolored).

The contingency table test for ordered categories showed a significant result (p <0.00004).
After 24 hours,
50% (n=6) of the yolk sacs (yolk vessel membranes) exhibited moderate and
50% (n=6) slight hemorrhaging in the case of the group treated with HP and with UV-A.

In contrast to this, the comparison samples only displayed slight hemorrhaging (with HP alone,
33.3% (n=4) exhibited slight hemorrhaging, in the case of a physiological saline solution and UV radiation,
25.0% (n=3) exhibited slight hemorrhaging;
and exclusively with a physiological saline solution,
16.7% (n=2) exhibited slight hemorrhaging).

The contingency table test for ordered categories indicated a significant result (p<0.00001).
Furthermore, it was found that, in
41.7% (n=5) of the HP/UV-A group, death of the embryo occurred. In contrast to this,
death of the embryo did not occur with any of the comparison samples.

Fisher's contingency table test showed a significant result (p<0.0094).

8-methoxypsoralen

The fundamental morphological changes were observed after a maximum of 12 hours. After 24 hours,
16.7% (n=2) of the yolk sacs exhibited severe,
75.0% (n=9) moderate and
8.3% (n=1) slight membrane discoloration in the 8-MOP/ UV-A group.

The comparison samples displayed slight to moderate membrane discoloration (with MOP alone,
58.3% (n=7) exhibited slight and
33.3% (n=4) moderate membrane discoloration;
in the group that had been treated with a physiological saline solution and UV-A,
50.0% (n=6) were found with slight discolored membranes, while in the comparison sample treated only a physiological saline solution,
41.7% (n=5) exhibited slight membrane discoloration and
16.7% (n=2) moderate membrane discoloration).

The contingency table test for ordered categories showed a significant result (p<0.00002).
After 24 hours,
91.7% (n=11) of the yolk sacs exhibited severe and
8.3% (n=1) moderate hemorrhaging with the 8-MOP/ UV-A group.

The comparison samples displayed only slight hemorrhaging (with 8-MOP alone, 16.7% (n=2) exhibited slight hemorrhaging;
in the group that had been treated with a physiological saline solution and UV-A,
8.3% (n=1) exhibited slight hemorrhaging;
in the group that had been treated only with a physical saline solution,
8.3% (n=1) exhibited slight hemorrhaging).

The contingency table test for ordered categories showed a significant result (p<0.00000).

For the 8-MOP/UV-A group, a lethality of 100% of the embryos (n=12) was observed.

In contrast to this, no deaths whatsoever were found with the comparison samples.

Fisher's contingency table test showed a significant result (p<0.00000).

Promethazine

Significant damage to the yolk sac membrane with a peak 12 hours after radiation was only observed in the case of promethazine (PMZ) in combination with UV-A radiation.

After 24 hours, 66.7% (n=8) of the yolk sacs exhibited severe,
8.3% (n=1) moderate and
25.0% (n=3) slight membrane discoloration in the PMZ/UV-A group.

The control samples only displayed slight or moderate membrane discoloration (with PMZ alone, 50.0% (n=6) exhibited slight membrane discoloration;
in the group that had been treated with a physiological saline solution and UV-A,
58.3% (n=7) exhibited slight membrane discoloration;
in the group that had been treated exclusively with a physiological saline solution,
58.3% (n=7) displayed slight membrane discoloration and
8.3% (n=1) moderate membrane discoloration).

The contingency table test for ordered categories showed a significant result (p <0.00005).

After 24 hours, 41.7% (n=5) of the yolk sac membranes exhibited severe,
41.7% (n=5) moderate and
8.3% (n=1) slight hemorrhaging, in the PMZ/UV-A group.

The control experiments only showed slight hemorrhaging (with PMZ alone, 8.3% (n=1) exhibited slight hemorrhaging;
with the use of a physiological saline solution and UV-A radiation,
8.3% (n=1) exhibited slight hemorrhaging;
with a physiological saline solution alone,
8.3% (n=1) exhibited slight hemorrhaging).

The contingency table test for ordered categories showed a significant result (p<0.00000).

After 24 hours,

100% of the embryos in the PMZ/UV-A group had died.

Only two dead embryos were found in the comparison groups (namely, in the group with a physiological saline solution and UV-A, 8.3% (n=1) as well as with the physiological saline solution alone,
8.3% (n=1)).

Fisher's contingency table test showed a significant result (p<0.00000).

Ciprofloxacin

Significant damage to the yolk vessel membrane was only found in a combination of ciprofloxacin (CF) with UV-A.

After 24 hours, 91.7% (n=11) of the yolk vessel membranes were severely discolored and
8.3% (n=1) of the membranes in the CF/UV-A group were moderately discolored.

In contrast to this, the comparison samples displayed slight and moderate membrane discoloration (with CF alone, 75.0% (n=9) exhibited slight membrane discoloration and
25.0% (n=3) moderate membrane discoloration;
in the group that had been treated with a physiological saline solution and UV-A,
66.7% (n=8) exhibited slight membrane discoloration and
8.3% (n=1) moderate membrane discoloration.

In the case of exclusive use of a physiological saline solution, 58.3% (n=7) exhibited slight membrane discoloration and
8.3% (n=1) moderate membrane discoloration).

The contingency table test for ordered categories had a significant result (p<0.00000).

After 24 hours, 50.0% (n=6) of the yolk vessel membrane displayed slight hemorrhaging and
16.7% (n=2) moderate hemorrhaging in the CF/UV-A group.

The comparison samples displayed only slight hemorrhaging (with CF alone, 41.7% (n=5) displayed slight hemorrhaging.

In the group treated with a physiological saline solution and UV-A, 25.0% (n=3) exhibited slight hemorrhaging;
in the group treated exclusively with a physiological saline solution 33.3% (n=4) displayed slight hemorrhaging).

These groups did not differ significantly from each other. No embryos died in any of the groups.

What is claimed is:

1. A process for determining the phytotoxicity and/or photosensitivity of substances or substance mixtures, comprising the steps of:

contacting the substance or substance mixture with non-human vertebrate embryo;
treating with radiation ranging from 1 mm to 200 nm; and
evaluating the embryo.

2. A process as claimed in claim 1, wherein the non-human vertebrate embryo comprises and egg of the Aves class.

3. A process as claimed in claim 1, wherein the substances or substance mixtures are selected from the group consisting of cosmetics, pharmaceuticals, herbicides, and insecticides.

4. A process as claimed in claim 1, wherein the radiation has a wavelength of less than 400 nm.

5. A process as claimed in claim 1, wherein the radiation is applied at a level ranging from 1 $mJ/cm^2$ to 100 $J/cm^2$.

6. A process as claimed in claim 1, wherein the contacting step is carried out for 10 seconds to 24 hours.

7. A process as claimed in claim 1, wherein the evaluation is macroscopic.

8. A process as claimed in claim 1, wherein the evaluation is microscopic.

9. A process as claimed in claim 1, wherein the evaluation examines death of the embryo, hemorrhaging, or membrane discoloration.

10. A process as claimed in claim 1, wherein the non-human vertebrate embryo comprises an egg of the Galliformes order.

11. A process as claimed in claim 1, wherein the substance is a chemical.

12. A process as claimed in claim 2, wherein openings are provided in the egg for contacting and treating.

13. A process as claimed in claim 4, wherein the radiation has a wavelength of 250 nm to 400 nm.

14. A process as claimed in claim 5, wherein the radiation level ranges from 1 to 20 $J/cm^2$ of UV-A.

15. A process as claimed in claim 5, wherein the radiation level ranges from 5 to 10 $J/cm^2$ of UV-A.

16. A process as claimed in claim 1, wherein the contacting step comprises contacting the substances or substance mixtures with yolk vessel membranes or chorioallantoic membranes of the embryo.

17. A process as claimed in claim 6, wherein the contacting step is carried out for 10 seconds to 24 hours.

18. A process as claimed in claim 10, wherein the egg is a chicken egg or turkey egg.

* * * * *